United States Patent [19]

Köhler et al.

[11] Patent Number: 5,237,041
[45] Date of Patent: Aug. 17, 1993

[54] PHOSPHORUS-CONTAINING DUROMERS OF OLIGOPHOSPHITES

[75] Inventors: Burkhard Köhler; Wolfgang Ebert, both of Krefeld, Fed. Rep. of Germany

[73] Assignee: Bayer Aktiengesellschaft, Leverkusen-Bayerwerk, Fed. Rep. of Germany

[21] Appl. No.: 982,891

[22] Filed: Nov. 30, 1992

[30] Foreign Application Priority Data

Dec. 9, 1991 [DE] Fed. Rep. of Germany ....... 4140543

[51] Int. Cl.$^5$ ............................................. C08G 63/692
[52] U.S. Cl. ..................... 528/272; 528/287; 528/296; 528/303; 528/308; 525/437; 525/438; 525/445; 525/447; 525/449; 525/451; 524/425; 524/765; 524/779; 522/13; 522/24; 558/70
[58] Field of Search ............... 528/272, 287, 296, 303, 528/308; 525/437, 438, 445, 447, 449, 451, 165; 524/425, 765, 779; 558/70; 522/24, 13

[56] References Cited

U.S. PATENT DOCUMENTS

| | | | |
|---|---|---|---|
| 3,158,642 | 11/1964 | Chapin et al. | 528/400 |
| 3,194,795 | 7/1965 | Friedman | 526/275 |
| 3,986,990 | 10/1976 | Giolito | 521/169 |
| 4,116,788 | 9/1978 | Schmitt et al. | 204/159.23 |
| 4,125,500 | 11/1978 | Mayer et al. | 524/119 |
| 4,125,501 | 11/1978 | Haberlein et al. | 524/117 |
| 4,293,472 | 10/1981 | Minagawa et al. | 524/289 |
| 4,463,112 | 7/1984 | Leistner et al. | 524/109 |
| 4,568,720 | 2/1986 | Aharoni et al. | 525/50 |

*Primary Examiner*—Samuel A. Acquah
*Attorney, Agent, or Firm*—Connolly and Hutz

[57] ABSTRACT

This invention relates to new phosphorus-containing duromers of oligophosphites and epoxides or bisacrylates or unsaturated polyesters.

2 Claims, No Drawings

PHOSPHORUS-CONTAINING DUROMERS OF OLIGOPHOSPHITES

The invention relates to new phosphorus-containing duromers of oligophosphites and epoxides or bisacrylates or unsaturated polyesters.

The reaction of spiro-bisphosphites containing phosphorous acid triesters groups with epoxy resins has been disclosed in EP-A 420 811. Brownish, duromeric moulding compounds were obtained.

The reaction of unsaturated compounds with diphosphites (diesters of phosphorous acid) for the preparation of polymers is known in principle.

Thus U.S. Pat. No. 31 94 795 teaches the preparation of a cyclic phosphite from trimethylolpropane monoallylether with triphenylphosphite followed by saponification of the cyclic triester and the polymerisation of this compound. A disadvantage of this process is that the reaction must be carried out in two stages in order to avoid the simultaneous presence of phosphorus-hydrogen bonds and allyl groups at elevated temperatures (spontaneous decomposition).

U.S. Pat. No. 31 58 642 describes the preparation of polyphosphine oxides from phenylphosphine and alkynes. Phenylphosphine is inflammable and the handling of alkynes at elevated temperatures under pressure is difficult.

The reaction of phosphorus-hydrogen bonds with unsaturated groups of tensioned small rings is of interest in spite of these difficulties as it enables duromers varying from rubber-like systems to rigid, flame-resistant materials to be obtained according to the choice of the starting materials. It would therefore be desirable to use starting materials which are readily synthesized and safe to handle.

It has now been found that mixtures of oligophosphites and unsaturated compounds of mixtures of oligophosphites and epoxides harden to form duromers.

The present invention therefore relates to duromers which are obtainable by the reaction of A) oligophosphites corresponding to formula I

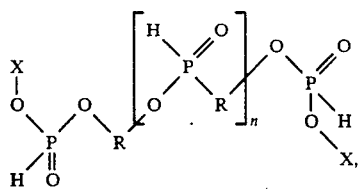

(I)

wherein

R denotes a $C_2$–$C_{44}$-alkylene group or corresponds to formula (II), (IV) or (V)

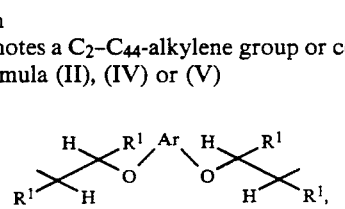

(II)

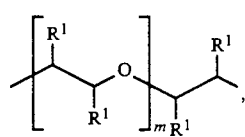

(IV)

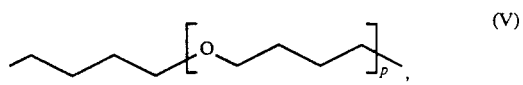

(V)

Ar stands for a $C_6$–$C_{14}$ arylene group or corresponds to formula (III)

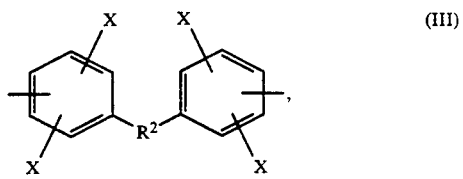

(III)

wherein $R^1$ stands for a $C_1$–$C_4$-alkyl group or hydrogen and the groups $R^1$ may be identical or different.

$R^2$ stands for a $C_1$14 $C_{12}$-alkylidene, a $C_6$–$C_{12}$-cycloalkylidene, a $C_2$–$C_{20}$-alkylene, an araliphatic, divalent $C_7$–$C_{26}$ group, an oxygen atom, a carbonyl group, a sulphur atom, a sulphone group or a chemical bond.

X stands for a $C_1$–$C_4$-alkyl group, m and p stand for natural numbers from 1 to 200 and n stands for a natural number from 1 to 20, or of oligophosphites obtainable by the reaction of dimethylphosphite or diethylphosphite or dipropylphosphites or dibutylphosphites with triols, each of which has two OH groups in the 1,2- or 1,3-position, optionally together with diols whose organic residue has the meaning of R or $R^1$, the oligophosphites thus obtained containing structural units corresponding to formulae (VI), (VII), (VIII) or (IX)

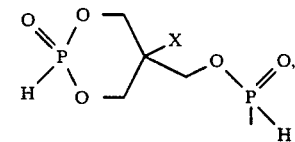

(VI)

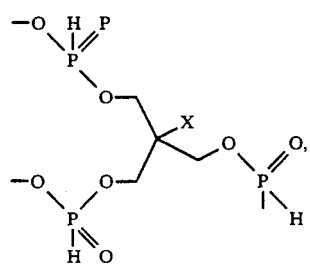

(VII)

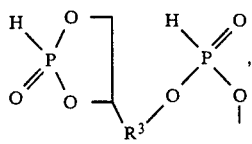

(VIII)

-continued

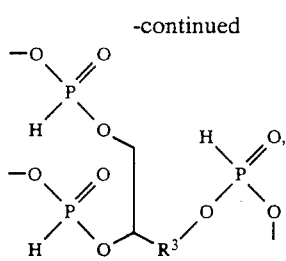
(IX)

and

R³ denotes a C₁C₁₂-alkylene group with

B1) polyunsaturated units such as, for example, unsaturated polyesters preferably containing maleic acid or fumaric acid ester units or allyl ether group-containing units as unsaturated units or acrylates or methacrylates of di- or polyols, or by the reaction of oligophosphites A with B2) di- or polyfunctional epoxides, from 0.7 to 5 equivalents of double bonds or epoxy groups being used for each phosphite equivalent.

The invention further relates to a process for the preparation of the duromers according to the invention, characterised in that the mixtures of oligophosphite A and polyunsaturated units B1) are hardened with from 0 to 5% by weight of basic catalysts such as hydroxides, carbonates or C₁-C₅-alcoholates of alkali metals or alkaline earth metals or with 0 to 5% by weight of initiators for radical reactions such as azo compounds or peroxy compounds, the basic catalysts being effective only for unsaturated polyesters containing maleic acid or fumaric acid ester units, or the mixtures of oligophosphites A) and epoxides B2) are hardened with from 0 to 5% by weight of basic catalysts such as hydroxides, carbonates or alcoholates of alkali metals or alkaline earth metals, hardening being carried out at temperatures from 80° C. to 220° C. for 0.1 to 10 hours.

The invention also relates to oligophosphites obtained by the reaction of diols whose organic residue has the meaning of R or R¹ with from two to ten times the molar quantity of dimethylphosphite, diethylphosphite, dipropylphosphites or dibutylphosphites in the presence of from 0.01 to 2% by weight of basic catalysts, preferably alkali metal carbonates, mot preferably potassium carbonate. In this reaction, the aliphatic alcohols which are formed from the dialkylphosphites are first distilled off at temperatures from 100° to 190° C., preferably at normal pressure, and dialkylphosphite is then distilled off at temperatures from 100° to 190° C., preferably at a reduced pressure of from 1 to 100 mbar.

The invention further relates to oligophosphites obtained by ther reaction of dimethylphosphite or diethylphosphite or dipropylphosphites or dibutylphosphites with triols having in each case two OH groups in the 1,2- or 1,3-positions to one another, optionally together with from 0 to 10 mol of diols, based on 1 mol of triol, the organic residues of which diols have the meaning of R and R¹, in the presence of from 0.01 to 2% by weight of basic catalysts, preferably alkali metal carbonates, most preferably potassium carbonate, the aliphatic alcohols formed from the dialkyl phosphites being first distilled off at temperatures from 100° to 190° C., preferably at normal pressure, and the dialkylphosphite being then distilled off at temperatures from 100° to 190° C., preferably at a reduced pressure of from 1 to 100 mbar, the molar ratio of diphosphite to the sum of triols+diols being from 10:1 to 3:1.

The epoxides used according to the invention are known and are described e.g. in Houben-Weyl, Methoden der organischen Chemie, Georg-Thieme-Verlag 1987, Volume E20/Part 3, pages 1891 to 1993. Glycidyl ethers of di- or polyphenols are preferred, e.g. glycidyl ethers of Novolaks.

The unsaturated polyesters used according to the invention are known and are described e.g. in Houben-Weyl, Methoden der organischen Chemie, Georg Thieme Verlag 1987, Volume E20/Part 2, pages 1414 to 1418. Maleic acid anhydride, fumaeric acid, neopentyl glycol, adipol, butylene glycol, ethylene glycol, diethylene glycol, phthalic acid anhydride, trimethylolpropane, propylene glycol, trimethylolpropane diallylether and adipic acid are preferred compounds for the polyester used according to the invention; at least one of the components present must be unsaturated.

The acrylates or methacrylates of di- or polyols used according to the invention are bisacrylates or bismethacrylates of adipol, diethylene glycol, butylene glycol or ethylene glycol or the triascrylates or trismethacrylates of trimethylolpropane or the tetrakisacrylates or tetrakismethacrylates of pentaerythritol.

The oligophosphites according to the invention are easy to prepare and safe owing to the moderate temperatures at which they are prepared.

The process according to the invention for the preparation of the duromers proceeds without any liberation of volatile by-products.

The duromers according to the invention are suitable for the production of optical articles such as optical fibres, elastomers and all products for which duromers are normally used.

EXAMPLES

Preparation Of The Phosphites

Example 1a 200 g of 2,2-bis-(4-hydroxyethyloxyphenyl)-propane (Dianol-22) are mixed with 200 g of diethylphosphite and 1 g of potassium carbonate. The mixture is heated to 160° C. for 6 hours, during which time ethanol distils off, among others. A water jet vacuum is then applied and the residue is heated to 120° C. for 2 hours, during which diethylphosphite distils off. 241 g of oligophosphite are obtained.

Example 2a 500 g of Polyethylene glycol having a molar mass of 400 g/mol are mixed with 300 g of diethylphosphite and 2 g of potassium carbonate. The mixture is heated to 160° C. for 6 hours, during which time ethanol distils off, among others components. A water jet vacuum is then applied and the residue is heated to 120° C. for 2 hours, during which diethylphosphite distils off. 585 g of oligophosphite are obtained.

Example 3a 1000 g of Polytetrahydrofuran having a molar mass of 2000 g/mol are mixed with 300 g of diethylphosphite and 4 g of potassium carbonate. The mixture is heated to 160° C. for 6 hours, during which time ethanol distils off, among others components. A water jet vacuum is then applied and the residue is heated to 120° C. for 2 hours, during which diethylphosphite distils off. 1090 g of oligophosphite are obtained.

Example 4a 135 g of Trimethylolpropane are mixed with 420 g of diethylphosphite and 2 g of potassium carbonate. The mixture is heated to 160° C. for 6hours, during which ethanol distils off, among other components. A water jet vacuum is then applied and the mixture is heated to 120° C. for 2 hours, during which diethylphosphite distils off. 199 g of oliogophosphites which may be branched and/or contain cyclic groups ar obtained.

Preparation Of The Unsaturated Polyester Used

Example 1b 173 g of Dimeric fatty acid, 294 g of maleic acid anhydride, 212.4 g of adipol, 187.2 g of neopentyl glycol, 0.3 g of dibutyl tin oxide and 0.6 g of hydroquinone are mixed together. The mixture is heated to 120° C. for 30 minutes, to 160° C. for 1.5 hours and to 210° C. for 4.5 hours. Water distils off in the process, among other components. 722 g of unsaturated polyester are obtained.

Preparation OF The Duromers

Example 1c 10 g of the Oligophosphite from Example 1a are mixed with 10 g of unsaturated polyester from Example 1b. The mixture is heated to 180° C. for 3 hours, 50 mg of a 30% sodium methanolate solution in methanol are added and the mixture is heated to 180° C., for 5 hours. A vitreous, insoluble mass having a glass temperature of 11° C. and a decomposition temperature of 369° C. (maximum of decomposition) is obtained.

Example 2c 10 g of the Oligophosphite from Example 1a are mixed with 6 g of adipol bisacrylate and the mixture is heated to 50° C. 0.5 g of Trigonox B (initiator of Akzo Company) is added and the mixture is then heated to 100° C., for 0.5 hours and to 170° C. for 2 hours. An opaque, white duromer mass having a glass temperature of 22° C. and a decomposition temperature of 361° C. (maximum of decomposition) is obtained.

Example 3c 10 g of the Oligophosphite from Example 2a are mixed with 10 g of Araldite PY 307 (Novolak epoxide of Ciba Company) and the mixture is heated to 160° C. 50 mg of 30% solution of sodium methanolate in methanol are added and the mixture is heated to 160° C., for one hour. A further 50 mg of the sodium methanolate solution is added and the resulting mixture is heated to 160° C. for 30 minutes. A rubber-like, transparent mass having a glass temperature of −21° C. and a decomposition temperature of 345° is obtained.

We claim:
1. Duromers obtainable by the reaction of
A) oligophosphites corresponding to formula I

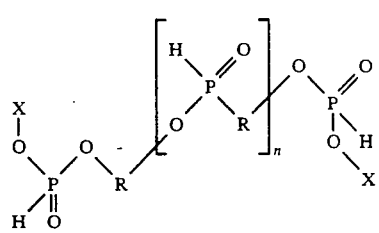

in which
R stands for a $C_2$-$C_{44}$-alkylene group or corresponds to formula (II), (IV) or (V)

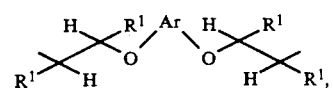

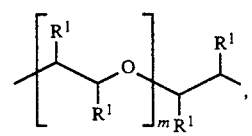

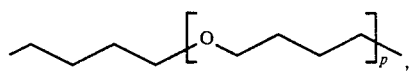

Ar stands for a $C_6$-$C_{14}$-arylene group or corresponds to formula (III)

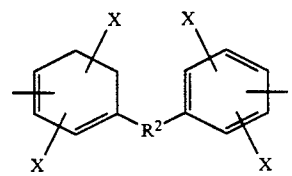

wherein
$R^1$ stands for a $C_1$-$C_4$-alkyl group or for hydrogen and the groups denoted by $R^1$ may be identical or different,
$R^2$ stands for a $C_1$-$C_{12}$-alkylidene, a $C_6$-$C_{12}$-cycloalkylidene or a $C_2$-$C_{20}$-alkylene group or an araliphatic, divalent $C_7$-$C_{20}$-alkylene group or analiphatic, divalent $C_7$-$C_{26}$-group, an oxygen atom, a carbonyl group, a sulphur atom, a sulphone group or a chemical bond,
X stands for a $C_1$-$C_4$-alkyl group,
m and p stand for natural numbers from 1 to 200 and
n stands for a natural number from 1 to 20,
or of oligophosphites obtained by the reaction of dimethylphosphite or diethylphosphite or dipropylphosphites or dibutylphosphites with triols in which two OH groups are in each case the 1,2- or 1,3-position to one another, optionally with the addition of diols whose organic residue corresponds to R or $R^1$, the oligophosphites thus obtained containing structural units corresponding to formulae (VI), (VII), (VIII) or (IX)

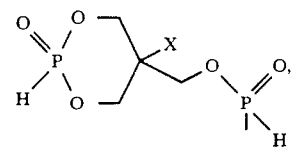
(VI)

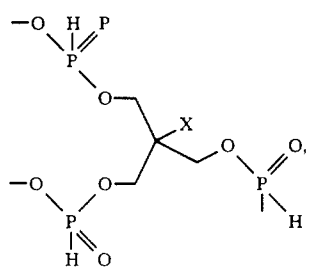
(VII)

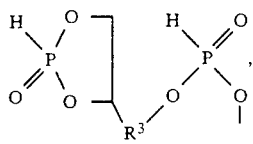
(VIII)

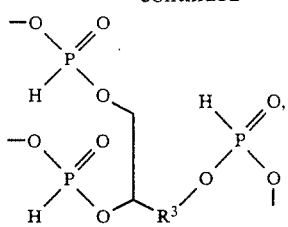
(IX)

and $R^3$ corresponds to a $C_1$–$C_{12}$-alkylene group with

B1) polyunsaturated units such as unsaturated polyesters containing maleic acid or fumaric acid ester units or allyl ether group-containing units as their unsaturated units, or acrylates or methacrylates of diols or polyols, or by the reaction of oligophosphites A with B2) difunctional or polyfunctional epoxides, from 0.7 to 5 equivalents of double bonds or epoxy groups being used for each phosphite equivalent.

2. A process for the preparation of the duromers according to claim 1, characterised in that the mixtures of oligophosphite A and polyunsaturated units B1) are hardened with from 0 to 5% by weight of basic catalysts such as hydroxides, carbonates or $C_1$–$C_5$-alcoholates of alkali metals or alkaline earth metals or with from 0 to 5% by weight of initiators for radical reactions such as azo compounds or peroxy compounds, the basic catalysts being effective only for unsaturated polyesters having maleic acid or fumaeric acid ester units, or the mixtures of oligophosphites A) and epoxides B2) are hardened with from 0 to 5% by weight of basic catalysts such as hydroxides, carbonates or alcoholates of alkali metals or alkaline earth metals, hardening being carried out at 80° C. to 220° C. for 0.1 to 10 hours.

* * * * *